US007732132B2

(12) United States Patent
Huang et al.

(10) Patent No.: US 7,732,132 B2
(45) Date of Patent: Jun. 8, 2010

(54) MONOCLONAL ANTIBODY TO THE COMMON EPITOPE OF NSS PROTEIN OF WATERMELON SILVER MOTTLE VIRUS AND ASSAY FOR TOSPOVIRUS

(75) Inventors: Ching-Wen Huang, Taichung (TW); Hei-Tu Hsu, Taichung (TW); Yan-Wen Kuo, Taichung (TW); Fang-Lin Liu, Taichung (TW); Chao-Hsiu Hsuan Yuan, Taichung (TW); Shyi-Dong Yeh, Taichung (TW); Tsung-Chi Chen, Taichung (TW)

(73) Assignee: National Chung Hsing University, Taichung (TW)

( * ) Notice: Subject to any disclaimer, the term of this patent is extended or adjusted under 35 U.S.C. 154(b) by 474 days.

(21) Appl. No.: 11/789,192

(22) Filed: Apr. 24, 2007

(65) Prior Publication Data

US 2009/0275013 A1 Nov. 5, 2009

(51) Int. Cl.
*C12Q 1/70* (2006.01)
*C12N 5/20* (2006.01)
*C07K 16/10* (2006.01)

(52) U.S. Cl. .............. 435/5; 435/331; 435/339; 530/387.9; 530/388.3

(58) Field of Classification Search ................ None
See application file for complete search history.

(56) References Cited

OTHER PUBLICATIONS

Chen et al (Phytopathology 96:1296-1304, Dec. 2006).*
Heinze et al (Journal of Virological Methods 89:137-146, 2000).*

* cited by examiner

*Primary Examiner*—Mary E Mosher
(74) *Attorney, Agent, or Firm*—Frenkel & Associates, PC

(57) ABSTRACT

The invention is an assay for detection of Watermelon silver mottle virus (WSMoV)-serogroup tospoviruses using a monoclonal antibody and a method for preparing the monoclonal antibody. A hybridoma cell line that produces a monoclonal antibody against the NSs proteins of WSMoV-serogroup tospoviruses was produced. The hybridoma cell line produces a monoclonal antibody binding with peptide SEQ ID No. 19.

4 Claims, 6 Drawing Sheets

```
WSMoV      89  . . . . . . . N.I . . . . . . . . . . . . . . . . . . . . . . . . . NI.N  125
PBNV       89  . . . . . . . . . . .V.G . . . . . . . . . . . . . . . . . . . . . . . .  125
CaCV       89  . . . . . . . . . . .V. . . . . I . . . . . . . . . S . . . . . . . G..S  125
CCSV       89  L.S.I.DII.T..N . . . . . . . . . . Q . . . . . . E . . . . .  125
Consensus      FCEHEMSL-VRKPGVKNTGCKFTMHNQIFNPNSDTLA
                                    ───────────────
                                        WNSscon
```

MONOCLONAL ANTIBODY TO THE COMMON EPITOPE OF NSS PROTEIN OF WATERMELON SILVER MOTTLE VIRUS AND ASSAY FOR TOSPOVIRUS

BACKGROUND OF THE INVENTION

1. Field of the Invention

The present invention relates to an assay for detection of Watermelon silver mottle virus serogroup in *Tospovirus* genus with monoclonal antibody and a method for preparing the monoclonal antibody.

2. Description of the Related Art

*Tospovirus* species belong to the genus *Tospovirus* are the only group of plant-infecting virus in the family Bunyaviridae. Tospoviruses are transmitted by thrips in a persistent manner and distributed worldwide to infect more than 900 species in 82 families of monocotyledonous and dicotyledonous plants. Virions of tospoviruses are enveloped quasi spherical particles containing three single-stranded RNAs of negative sense and ambisense. Owing to the instability of tospoviruses, it is difficult to purify sufficient amounts of their individual proteins.

The tropical and subtropical climate in South Asia and Eastern South Asia is adaptable for the growth and survival of thrips, the vector of tospoviruses. The Watermelon silver mottle virus (WSMoV)-serogroup tospoviruses are the major species distribute over these areas. The reported members in the WSMoV serogroup, based on the serological relationship of nucleocapsid protein (NP), include WSMoV and Calla lily chlorotic spot virus (CCSV) in Taiwan, Peanut bud necrosis virus (PBNV) and Watermelon bud necrosis virus (WBNV) in India, and Capsicum chlorosis virus (CaCV) in Australia and Thailand.

Due to the convenience of international transportation and the frequency of agricultural transaction among various countries, tospoviruses or their vectors are easily to be inadvertently imported. Therefore, the quarantine of agricultural products tends to important. Development of a fast and precise examination system will be useful to understand and monitor the distribution of tospoviruses for promoting agriculture competition in the international market.

SUMMARY OF THE INVENTION

In one aspect, the invention is a hybridoma cell line deposited under CCTCC accession number 200718.

Preferably, the hybridoma cell line produces a monoclonal antibody against the common epitope of the NSs protein of Watermelon silver mottle virus (WSMoV).

Preferably, the hybridoma cell line produces a monoclonal antibody binding with peptide SEQ ID No. 19.

In another aspect, the invention is a monoclonal antibody binding with peptide SEQ ID No. 19.

Preferably, the monoclonal antibody is produced by the above hybridoma cell line.

In another aspect, preparation of an antiserum for detection of the WSMoV-serogroup tospoviruses comprises providing an immunogen including peptide SEQ ID No.19:

injecting the immunogen in an animal subcutaneously to induce an immune reaction; and obtaining antiserum from the animal.

Preferably, a concentration of the immunogen is in the range of 50 μg to 1 mg.

Preferably, the concentration of the immunogen is about 100 μg peptide SEQ ID No.19.

Preferably, the immunogen is emulsified with an equal volume of Freund's complete adjuvant and injected subcutaneously into the animal one time.

Preferably, the immunogen is emulsified with an equal volume of Freund's incomplete adjuvant and is administered weekly for three times after the first injection.

In another aspect, a kit for detection of WSMoV serogroup in the genus *Tospovirus* comprises the above monoclonal antibody.

Preferably, the kit is a serological analysis kit.

Preferably, the kit comprises a secondary antibody, washing solution and chromogenic substrate.

More preferably, the secondary antibody is alkaline phosphatase (AP)-conjugated goat-anti-rabbit IgG or AP-conjugated goat anti-mouse IgG.

In another aspect, a method for producing the above hybridoma cell line comprises providing an immunogen including the NSs protein of WSMoV of the genus *Tospovirus;* injecting the NSs protein in an animal intraperitoneally to induce an immune reaction;

getting spleen cells and fusing spleen cells with myeloma cells; and selecting hybridoma cells producing an anti-immunogen antibody.

Preferably, the NSs protein is cloned into a vector and expressed in the eukaryotic cell system.

More preferably, the eukaryotic cells are plant cells.

More preferably, the vector is Zucchini yellow mosaic virus (ZYMV).

More preferably, the NSs protein has a histidine tag at the C-terminal end.

In another aspect, an assay for the detection of the WSMoV-serogroup tospoviruses comprises providing a sample;

contacting the sample with the monoclonal antibody as described previously; and testing via an immunoassay;

wherein when the result is positive, the sample is infected by the WSMoV-serogroup tospoviruses; and when the result is negative, the sample is not infected by the WSMoV-serogroup tospoviruses.

Preferably, the immunoassay is an immunodiffusion assay, enzyme-linked immunosorbent assay, tissue blot immunoassay, fluorescence immunoassay or immunosorbent-electron microscopy.

Other objectives, advantages and novel features of the invention will become more apparent from the following detailed description when taken in conjunction with the accompanying drawings.

BRIEF DESCRIPTION OF THE DRAWINGS

FIG. 2 is a polyacrylamide gel electrophoresis showing purification of NSs proteins from the ZWSMoV-NSs-infected zucchini squash plants by affinity chromatography;

FIG. 4 is a diagram of different constructs containing various deletions of NSs open reading frames (ORFs) expressed by the ZYMV vector for epitope mapping;

FIG. 5 is a diagram of comparison of the monoclonal antibody-targeting region of WSMoV NSs protein with those of tospoviruses in WSMoV serogroup, wherein the target region of WSMoV NSs protein includes a peptide having the sequence set forth in SEQ ID NO: 19; and FIG. 6 is a polyacrylamide gel electrophoresis for confirmation of the epitopes in the NSs proteins of the WSMoV-serogroup tospoviruses by western blotting.

DETAILED DESCRIPTION OF THE PREFERRED EMBODIMENTS

Figure 1:
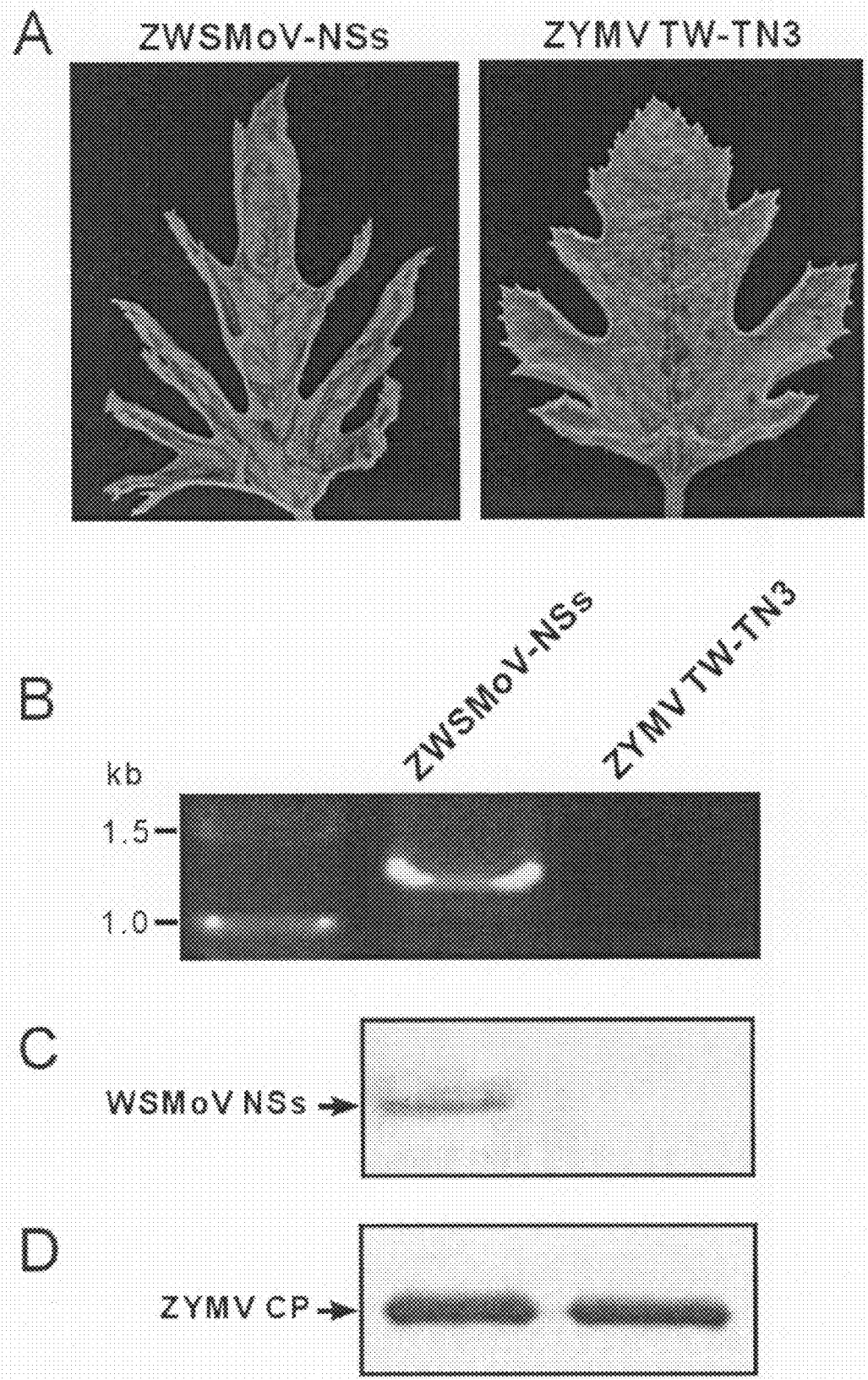
FIG. 1 A is a photograph of leaves of ZWSMoV-NSs- or wild type ZYMV TW-TN3-infected plants 14 days post-inoculation (dpi); B is an agarose gel electrophoresis that confirms the presence of the insert in the recombinant by reverse transcription-polymerase chain reaction (RT-PCR); C is a polyacrylamide gel electrophoresis monitoring the NSs protein expression by western blotting and D is a polyacrylamide gel electrophoresis that confirms the presence of the recombinant by the antiserum to the ZYMV coat protein (CP) by western blotting.

WSMoV is a member of the genus *Tospovirus* that limits production of cucurbits in Taiwan. Purification of tospoviral proteins except nucleocapsid protein (NP) from the infected plants is difficult. Therefore, the ORF of the nonstructural (NSs) protein of WSMoV was cloned and inserted in between the P1 and HC-Pro cistrons of the ZYMV vector. The expressed NSs protein with six histidine residues as tag and an additional NIa protease cleavage sequence at the C-terminus, so that the free-form NSs protein was isolated by $Ni^{2+}$-NTA resins and further eluted after sodium dodecyl sulfate-polyacrylamide gel electrophoresis (SDS-PAGE) for production of rabbit antiserum and mouse monoclonal antibody (MAb). The rabbit antiserum strongly reacted with the NSs crude antigen of WSMoV and weakly with CaCV, but not with that of CCSV. In contrast, the MAb reacted strongly with all crude NSs antigens of WSMoV, CaCV and CCSV. Various deletions of the NSs ORF were constructed and expressed by the ZYMV vector. Our results indicate that MAb targets at the amino acid (aa) 89 to 125 region of WSMoV NSs protein. Two indispensable residues of cysteine and lysine were essential for MAb recognition. Sequence comparison of the deduced MAb-recognized region with the reported tospoviral NSs proteins revealed the presence of a consensus sequence VRKPGVKNTGCKFTMHNQIFNPN (denoted WNSscon), at the aa 98 to 120 position of NSs proteins, sharing 86 to 100% identities among those of WSMoV, CaCV, CCSV and PBNV. A synthetic WNSscon peptide reacted with the MAb and verified that the epitopes are present in the aa 98 to 120 region of WSMoV NSs protein having the sequence set forth in SEQ ID NO: 19. The WSMoV serogroup-specific NSs MAb provides a means for reliable identification of tospoviruses in this large serogroup.

The term "immunogen" used in accordance with the present invention refers to a substance that causes an immune response in an animal.

The term "kit" used in accordance with the present invention further comprises a solid support and a chromogenic substrate. The solid support can be coated protein and may be a micro well plate, latex beads, membrane filter paper, glass and metal. The chromogenic substrate may be radioactivity, enzyme, phosphate, biotin or fluorogenic reactions.

The term "sample" used in accordance with the present invention may be an extract of plant tissue or a plant cell. Preferably, the plant tissue is a leaf.

The term "monoclonal antibody" used in accordance with the present invention refers to an antibody obtained by a single clone of B cells and thus consisting of a population of homogeneous antibodies.

The term "serogroup" used in accordance with the present invention refers to a group differing from others on immunological criteria.

The term "animal" used in accordance with the present invention is mammal. Preferably, mammal is rabbit or mouse.

EXAMPLE

Example 1

Source and Culture of Tospoviruses

Watermelon silver mottle virus (WSMoV) (50) and a newly reported CCSV isolated from calla lilies (5) were collected from Taiwan. A high temperature-recovered gloxinia isolate (HT-1) of CaCV from the United States was previously reported (21). These three viruses are classified in the WSMoV serogroup (24, 38). Tomato spotted wilt virus (TSWV), a type member of TSWV serogroup isolated from tomato in New York (TSWV-NY) was provided by R. Provvidenti, New York State Experiment Station, Geneva. An isolate of Groundnut ringspot virus (GRSV) collected from infected tomato in Brazil was provided by D. Gonsalves, New York State Experiment Agricultural Station (39). Impatiens necrotic spot virus (INSV) isolated from impatiens in the United States (INSV-M) was provided by J. Moyer, North Carolina State University, Raleigh (30). Peanut chlorotic fanspot virus (PCFV) was isolated from peanuts in Taiwan (9). All virus cultures were maintained in the systemic host *Nicotiana benthamiana* Domin. and the local lesion host *Chenopodium quinoa* Willd. by mechanical transmission. The TW-TN3 isolate of Zucchini yellow mosaic virus (ZYMV TW-TN3) (37) was maintained in the systemic host zucchini squash (*Cucurbita pepo* L.) and the local lesion host *C. quinoa*.

Example 2

Production of Rabbit Antiserum and Mouse MAb Against the Nonstructural (NSs) protein of WSMoV 2.1 Expression of NSs Protein The full-length NSs ORF was amplified from WSMoV S RNA using primers WNSs67KS (SEQ ID No.1) and WNSs1383cK (SEQ ID No. 2) by RT-PCR and was cloned into pCR2.1-TOPO by TOPO TA Cloning Kit (Invitrogen, Carlsbad, Calif.) to generate pTOPO-WNSs. The DNA fragment corresponding to NSs ORF was released from pTOPO-WNSs using restriction enzymes SphI and KpnI and then ligated with the SphI/KpnI-digested ZYMV vector p35SZYMVGFPhis (6,18). The plasmid of the ZYMV recombinant carrying NSs ORF was isolated by the mini-prep method (41), dissolved in TE buffer (10 mM Tris-HCl and 1 mM EDTA, pH 8.0) and mechanically introduced with a glass spatula on *C. quinoa* leaves (10 μg in 10 μl per leaf) dusted with 600 mesh carborundum. Developed local lesions were individually transferred onto cotyledons of zucchini squash plants (6). Total RNAs were extracted from symptomatic zucchini squash leaves using the ULTRASPEC RNA isolation system (Biotex Laboratories, Houston, Tex.), and primers WNSs67KS (SEQ ID No.1) and WNSs1383cK (SEQ ID No. 2) were used to check the presence of the insert in the recombinant by RT-PCR. PCR products were analyzed in 1.0% agarose gels by electrophoresis.

2.2 Purification of the Expressed NSs Protein

A method of affinity chromatography (12) was modified for purification of the ZYMV-expressed NSs protein from infected zucchini squash plants. Fifty grams of infected squash leaves were ground in 100 ml of buffer A [50 mM Tris-HCl, pH 8.0, 15 mM $MgCl_2$, 10 mM KCl, 20% (v/v) glycerol, 0.05% β-mercaptoethanol, and 0.1 mM phenylmethylsulphonyl fluoride (PMSF)] in a blender. Extracts were clarified by centrifugation at 3,000×g for 10 minutes, and supernatants were filtered through Miracloth (Calbiochem, La Jolla, Calif.). The filtrates, treated with 1% Triton X-100 at 4° C. for 30 min, were centrifuged at 30,000×g for 30 minutes. The supernatants were filtered through 0.45 μm filters (Millipore, Billerica, Mass.). Approximately 1 ml of $Ni^{2+}$-NTA resin (Ni-NTA SUPERFLOW, Qiagen, Germany) pre-equilibrated in buffer B [50 mM Tris-HCl, pH 8.2, 15 mM $MgCl_2$, 20% (v/v) glycerol, 0.05% β-mercaptoethanol, and 0.1 mM PMSF] were added. The mixtures were gently shaken for 1 hour at 4° C. and loaded onto a column. After allowing the resin to settle, the unbound materials were discarded and the resin was washed with 2-fold bed volume of buffer B containing 5 mM imidazole. The proteins bound to the resins were eluted with 10 ml of buffer B containing 250 mM imidazole. The NSs protein was further purified by gel electrophoresis method (49).

3. Production of Rabbit Antiserum

Antiserum was produced by injecting the purified ZYMV-expressed WSMoV NSs protein into a New Zealand white rabbit as described (49). The NSs protein (100 μg in 1 ml of phosphate-buffered saline, PBS) was emulsified with an equal volume of Freund's complete adjuvant (Difco Laboratories, BD, Franklin Lakes, N.J.) and injected subcutaneously into the rabbit. Subsequently, 100 μg of the immunogen in 1 ml PBS emulsified with an equal volume of Freund's incomplete adjuvant (Difco Laboratories) was administered weekly for three times. The rabbit was bled weekly for two months, starting from one week after the fourth injection.

4. Production of Mouse Monoclonal Antibody and Ascitic Fluids

Fifty micrograms of purified NSs protein in 250 μl PBS emulsified with an equal volume of Freund's complete adjuvant (Difco Laboratories) was intraperitoneally injected into 6 to 8 weeks old female BALB/cByJ mice (Academia Sinica, Taipei). The same amount of immunogen emulsified with Freund's incomplete adjuvant (Difco Laboratories) was used for two subsequent weekly intraperitoneal injections. Mice were sacrificed 3 days after a final injection with 50 μg purified NSs protein in 250 μl PBS without adjuvant, and spleen cells were harvested for cell fusion with Fox-NY myeloma cells (American Type Culture Collection, Manassas, Va. 20108) following a method described previously (20). After fusion, cells were cultured in a 37° C. incubator supplied with 6% $CO_2$. Cultured media were collected and screened for anti-NSs antibodies by indirect ELISA using crude extracts prepared from leaf tissues of N. benthamiana plants infected with WSMoV. Subsequently, the antibody-secreting hybridoma cells were cloned by limiting dilution. Stable hybridoma cell lines were selected after three cycles of cloning. Pristane-primed BALB/cByJ mice were intraperitoneally injected with $1.0×10^6$ hybridoma cells each for production of ascitic fluids (19).

5. Western Blot

Protein expression and purification, yield estimation of purified NSs protein and virus detection were all monitored by western blotting as described (15). Crude extracts from leaves of tospovirus-infected N. benthamiana plants were analyzed at a 50-fold dilution in dissociation buffer (100 mM Tris-HCl, pH 7.2, 2% β-mercaptoethanol, 10% sucrose, 0.005% bromophenol blue, and 10 mM EDTA). Crude extracts of zucchini squash infected with wild type ZYMV TW-TN3 or its recombinants were diluted to 20 fold in dissociation buffer. MAb-His (Amersham Pharmacia Biotech) was used at a $5.0×10^{-4}$ dilution to detect the ZYMV-expressed WSMoV NSs protein. The rabbit antiserum to ZYMV CP (37) was used at a $2.5×10^{-4}$ dilution to confirm infection by the recombinants. Ascitic fluid containing MAbs to WSMoV NP (134B1A8) or CCSVNP (335F9E7)(38) was used at a $1.0×10^{-5}$ dilution to verify the presence of tospoviruses. The alkaline phosphatase (AP)-conjugated goat anti-rabbit IgG (Jackson ImmunoResearch Laboratories, West Grove, Pa.) and the AP-conjugated goat anti-mouse IgG (Jackson ImmunoResearch Laboratories) were used at a $2.0×10^{-4}$ dilution as the secondary antibody for detection of rabbit and mouse antibodies, respectively. Reactions were visualized by the addition of chromogenic substrate (nitro-blue tetrazolium/5-bromo-4-chloro-3-indolyl phosphate para-toluidine salt in 100 mM NaCl, 5 mM $MgCl_2$, and 100 mM Tris-HCl, pH 9.5).

6. Indirect ELISA

Indirect ELISA was employed according to a method described previously (49). Either 100-fold diluted crude extracts of tospovirus-infected N. benthamiana or 20-fold diluted crude extracts of ZYMV recombinant-infected zucchini squash were used as coating antigens. Cell culture media at a ½ dilution were used for screening antibody-secreting hybridoma cell lines. Ten-fold serial dilutions starting from a $1.0×10^{-3}$ dilution of the rabbit antiserum or ascitic fluids were used for titration. The AP-conjugated goat anti-mouse IgG and the AP-conjugated goat anti-rabbit IgG was used at a $2.0×10^{-4}$ dilution as the secondary antibody for detection of mouse and rabbit antibodies, respectively. The absorbance at 405 nm ($A_{405}$) was determined using an EL×800 universal microplate reader (Bio-Tek instrument, Winooski, Vt.) 10 to 40 min after the addition of AP substrate (Sigma 104; Sigma-Aldrich Fine Chemicals, Milwaukee, Wis.).

7. Epitope Scanning of MAb

DNA fragments corresponding to different portions of the NSs ORF were amplified by PCR using pTOPO-WNSs as a template. Sequences of individual primers used for amplification are listed in Table 1. The protocol of denaturing at 94° C. for 30 seconds, reannealing at 58° C. for 30 seconds and synthesis at 72° C. for 1 minute for 30 cycles, with a final reaction at 72° C. for 7 minutes, was used for PCR. Individual DNA fragments corresponding to deleted NSs ORFs were cloned into pCR2.1-TOPO by TOPO TA Cloning Kit (Invitrogen) for sequence confirmation. DNA fragments were released from pCR2.1-TOPO using restriction enzymes SphI and KpnI and then ligated with the SphI/KpnI-digested ZYMV vector p35SZYMVGFPhis as previously described (6,18). The individual ZYMV recombinants derived from each plasmid were recovered from C. quinoa and zucchini squash similar to the procedure described for the recombinant expressing the full-length NSs protein.

8. Synthesis of Peptide and Production of Antiserum

To confirm the common epitopes identified by the produced MAb, a 23-amino acid peptide (VRKPGVKNTGCK-FTMHNQIFNPN, SEQ ID No. 19) denoted as WNSscon coupled with multiple antigen peptides (MAP) was synthesized by PTI Symphony (Protein Technologies, Inc., Tucson, Ariz.). The synthetic WNSscon peptide of 0.2 μg was analyzed by 15% SDS-PAGE, transferred to membranes and reacted with the rabbit antiserum diluted at $1.0 \times 10^{-3}$ and mouse MAb diluted at $1.0 \times 10^{-5}$ in western blotting. The synthetic WNSscon peptide also was injected into a New Zealand white rabbit to produce antiserum as described above.

9. Results 9.1 Establishment of the ZYMV Recombinant Expressing WSMoV NSs Protein A cDNA construct of ZYMV chimera carrying the full-length WSMoV NSs ORF was obtained and denoted p35SZWSMoV-NSs. The recombinant ZWSMoV-NSs derived from p35SZWSMoV-NSs induced typical local lesions on inoculated *C. quinoa* leaves and caused severe systemic symptoms of yellow mosaic and leaf distortion on zucchini squash plants 10 to 14 days post-inoculation (dpi) (FIG. 1A). The presence of ZWSMoV-NSs was confirmed by an RT-PCR product of 1.3 kb, corresponding to the complete NSs ORF that was amplified with primers WNSs67KS and WNSs1383cK (FIG. 1B). A protein of 52.2 kDa, containing additional residues of a histidine tag, proteolytic and cloning sites, slightly larger than the native WSMoV NSs protein (49.7 kDa) was detected in the ZWSMoV-NSs-infected squash plants by western blotting using MAb-His (FIG. 1C). In addition, ZYMV CP (31.3 kDa) was detected in the ZWSMoV-NSs-infected squash plants by western blotting using the rabbit antiserum to the CP of ZYMV (FIG. 1D).

9.2 Purification of the Expressed NSs Protein

Figure 2:
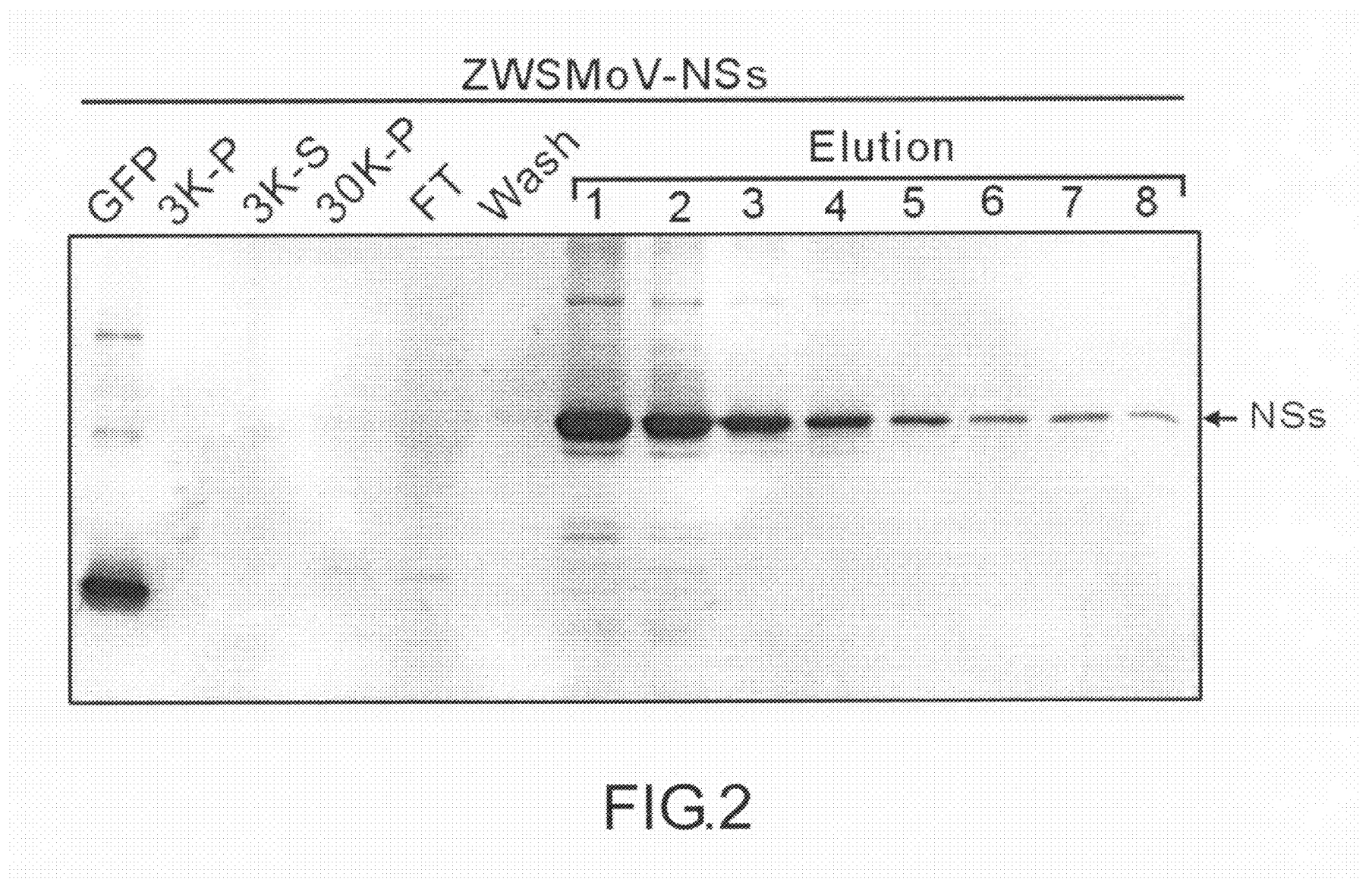

Each step for purification of ZYMV-expressed NSs protein from infected squash tissues was analyzed by western blotting using MAb-His. A protein of 52.2 kDa in elution fractions was pooled and identified as the ZYMV-expressed NSs protein by MAb-His (FIG. 2). A trace amount of a larger protein of 104 kDa was also obtained. Proteins eluted from $Ni^{2+}$-NTA resins were further separated by gel electrophoresis to remove other plant proteins. An estimated 470 μg of purified NSs protein was obtained from 100 g ZWSMoV-NSs-infected squash tissues by comparing with standardized histidine-tagged GFP in western blotting and quantified BSA in SDS-PAGE, and estimated by the Spot Density of AlphaInnotech IS2000.

9.3 Production of Antibodies

The purified NSs protein was used as an immunogen for production of rabbit polyclonal antibody (PAb) and mouse MAb. Antiserum produced from the immunized rabbit has a dilution endpoint of $1.0 \times 10^{-5}$ as determined by ELISA. The antiserum was used at a $1.0 \times 10^{-3}$ dilution in further investigations.

Additionally, the stable hybridoma cell line WNSs 239F1A8 was established by limiting dilution and deposited under the provisions of the Budapest Treaty with the CCTCC accession number 200718, on Feb. 14, 2007, with the description of the cell line at China Center For Type Culture Collection, Wuhan University, Wuhan 430072 P.R. China. Hybridoma cells were injected intraperitoneally into Pristane-primed mice for production of ascitic fluids. The dilution endpoints of ascitic fluids from WNSs 239F1A8 are $1.0 \times 10^{-8}$ and are used at a $1.0 \times 10^{-5}$ dilution for further studies.

9.4 Serological Reactions of Rabbit Antiserum and Mouse Ascitic Fluids

Figure 3:
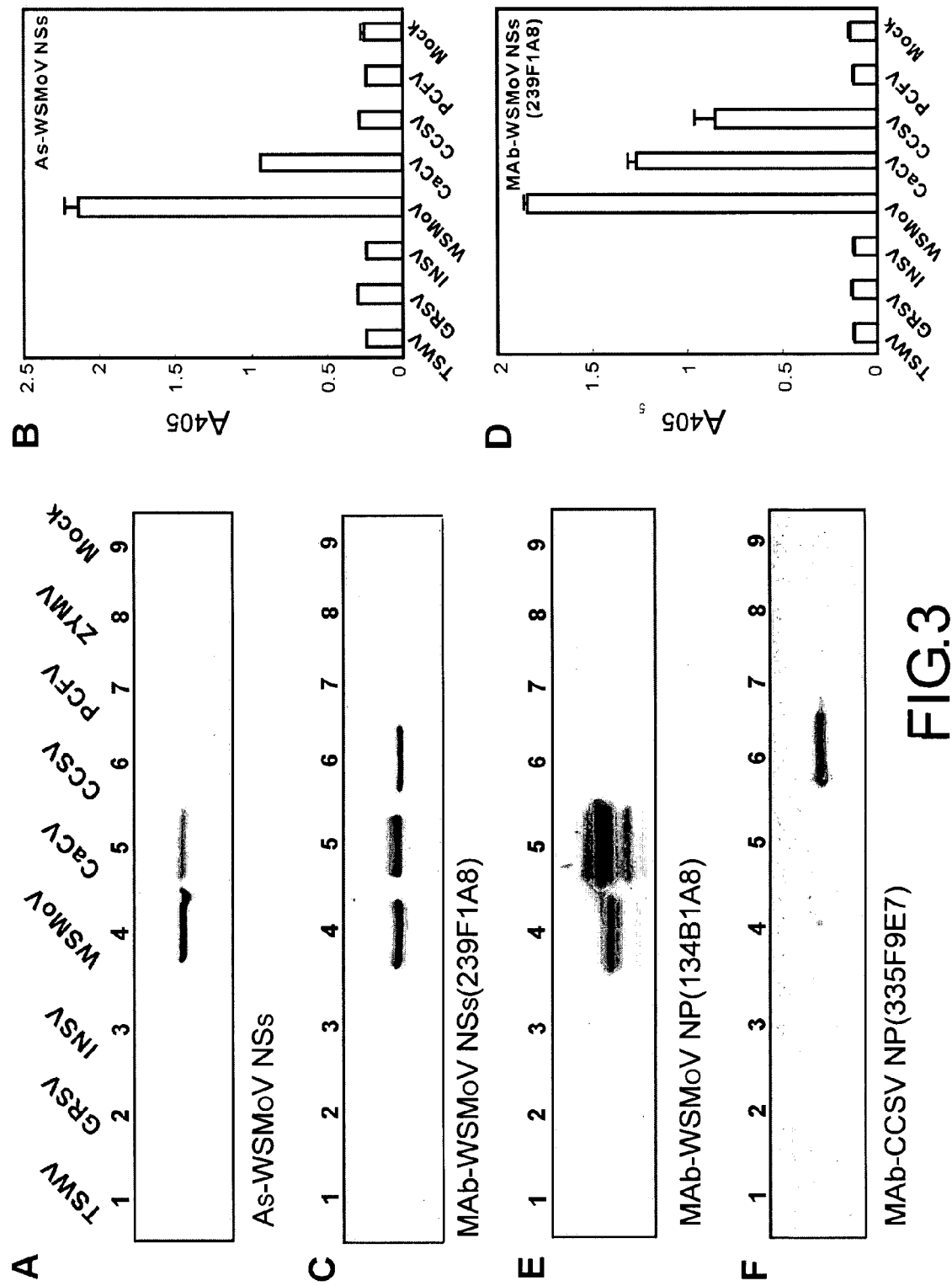
FIGS. 3 A and C are polyacrylamide gel electrophoresis of a rabbit antiserum and a mouse monoclonal antibody, respectively, reacted with the NSs proteins of different tospoviruses in western blotting; B and D are diagrams of a rabbit antiserum and a mouse monoclonal antibody, respectively, reacted with the NSs proteins of different tospoviruses in indirect ELISA; and E and F are polyacrylamide gel electrophoresis of mouse monoclonal antibodies reacted with the NPs of WSMoV and CCSV, respectively.

The rabbit antiserum reacted strongly with the NSs protein in the crude extracts of WSMoV-infected plants of *N. benthamiana* and *C. quinoa* and weakly with the crude extracts of CaCV-infected samples, but did not react with samples of TSWV, GRSV, INSV, CCSV, PCFV and ZYMV TW-TN3 in western blotting (FIG. 3A). In indirect ELISA, the average readings of WSMoV (2.14) and CaCV (0.93) were 8.4- and 3.7-fold, respectively, higher than that (0.25) of a mock control, but the average readings (0.24 to 0.29) of TSWV, GRSV, INSV, CCSV and PCFV were not significantly different (defined as two-fold higher) from that of the mock control (FIG. 3B).

Ascitic fluids produced from WNSs239F1A8 reacted positively with crude extracts of *N. benthamiana* and *C. quinoa* plants individually inoculated with WSMoV, CaCV or CCSV, but not with those from plants infected with TSWV, GRSV, INSV, PCFV or ZYMV TW-TN3 in western blotting (FIG. 3C). In indirect ELISA, the MAb also reacted with crude antigens of WSMoV (an average reading of 1.84), CaCV (1.27) and CCSV (0.85), with readings 13.2-, 9.1- and 6.1-fold higher than that (0.14) of the mock control, respectively; but not with those of TSWV (0.12), GRSV (0.13), INSV (0.12) and PCFV (0.13) (FIG. 3D). The identity and the presence of the tested tospoviruses were checked by MAb specific to the NP of WSMoV or CCSV in western blotting. WSMoV NP MAb 134B1A8 identified WSMoV and CaCV (FIG. 3E); whereas CCSVNP MAb 335F9E7 identified CCSV (FIG. 3F).

Consequently, the MAb from the hybridoma cell line WNSs239F1A8 recognizes common epitopes present on the NSs molecules of WSMoV, CaCV and CCSV. However, the rabbit antiserum did not react with the NSs protein of CCSV because the presence of a major population of IgG targets on epitopes, which are different from those targeted by the MAb. Results from present studies of serological analysis indicate that CaCV is closely, but CCSV is distantly, related to WSMoV, and yet they share common antigenic determinants revealed by the MAb.

9.5 Determination of the MAb-recognized Region

Figure 4:
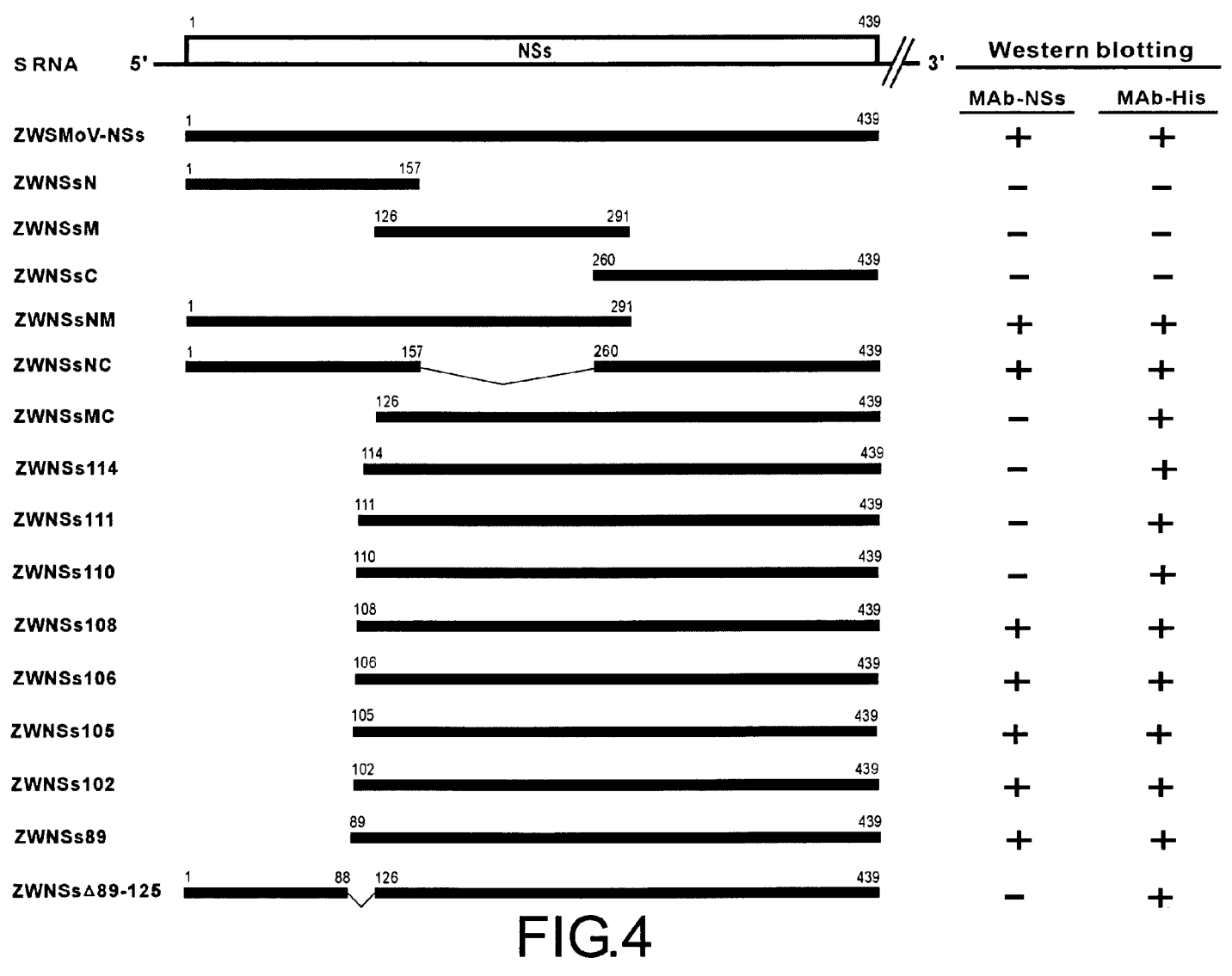

DNA fragments corresponding to different portions of the WSMoV NSs ORF were introduced into the ZYMV vector for expression of various truncated NSs proteins. The regions of NSs ORF expressed and their corresponding serological reactions with the WSMoV NSs and His MAbs in western blotting are shown in FIG. 4. The ZYMV recombinants expressing the N-terminal region (aa 1 to 157), the middle region (aa 126 to 291), the C-terminal region (aa 260 to 439), the N-terminal to middle region (aa 1 to 291), the middle to C-terminal region (aa 126 to 439) and the fused N-terminal region (aa 1 to 157) and C-terminal region (aa 260 to 439) of the WSMoV NSs protein were denoted ZWNSsN, ZWNSsM, ZWNSsC, ZWNSsNM, ZWNSsMC and ZWNSsNC, respectively. Positive reactions with the MAb from hybridoma cell line WNSs239F1A8 was observed in samples of ZWNSsNM and ZWNSsNC, but not in those of ZWNSsN, ZWNSsM, ZWNSsC and ZWNSsMC, indicating that the NSs MAb target the N-terminal region of the WSMoV NSs protein.

Based on the above results, recombinants expressing NSs proteins with various deletions in the N-terminal extensions were constructed. Samples of ZWNSs114, ZWNSs111 and ZWNSs110 expressing the aa 114 to 439, the aa 111 to 439 and the aa 110 to 439 of the NSs protein, respectively, did not react with the MAb. However, the MAb reacted positively with samples of ZWNSs108, ZWNSs106, ZWNSs105, ZWNSs102 and ZWNSs89 expressing the aa 108 to 439, the aa 106 to 439, the aa 105 to 439, the aa 102 to 439, and the aa 89 to 439 of the NSs protein, respectively. In addition, two DNA fragments corresponding to the nt 67 to 330 and nt 442 to 1383 of WSMoV S RNA were ligated to generate the aa 89 to 125 deleted NSs protein that was expressed by the recombinant ZWNSsΔ89-125. This 89 to 125 deleted NSs protein reacted with MAb-His, but did not react with the MAb. All these results indicated that the epitopes recognized by the MAb were located within the region of aa 89 to 125 of the NSs protein, and that the aa 108 to 109, $C_{108}$ and $K_{109}$, are two indispensable residues for the reactivity of the protein.

9.6 Comparison of the MAb-targeted Region with the NSs Proteins Among Members of WSMoV Serogroup Amino acid sequences of the NSs proteins of CCSV, CaCV, PBNV and WSMoV were compared. A consensus sequence SEQ ID No.19 (VRKPGVKNTGCKFTMHNQIFNPN) present in the MAbs-targeted region at the position of aa 98 to 120 of WSMoV NSs protein, sharing high identities of 95%, 91% and 86% with those of PBNV, CaCV and CCSV, respectively, was noticed (FIG. 5).

9.7 Serological Confirmation of the MAb-recognized Region

A 23 aa of WNSscon peptide (VRKPGVKNTGCKFTM-HNQIFNPN, SEQ ID No.19) that reflects the aa 98 to 120 of WSMoV NSs protein was synthesized to test the reactivity of the rabbit antiserum and the mouse MAb by western blotting. Mouse MAb reacted with the synthetic peptide, but the rabbit antiserum did not (FIG. 6A).

Figure 6:
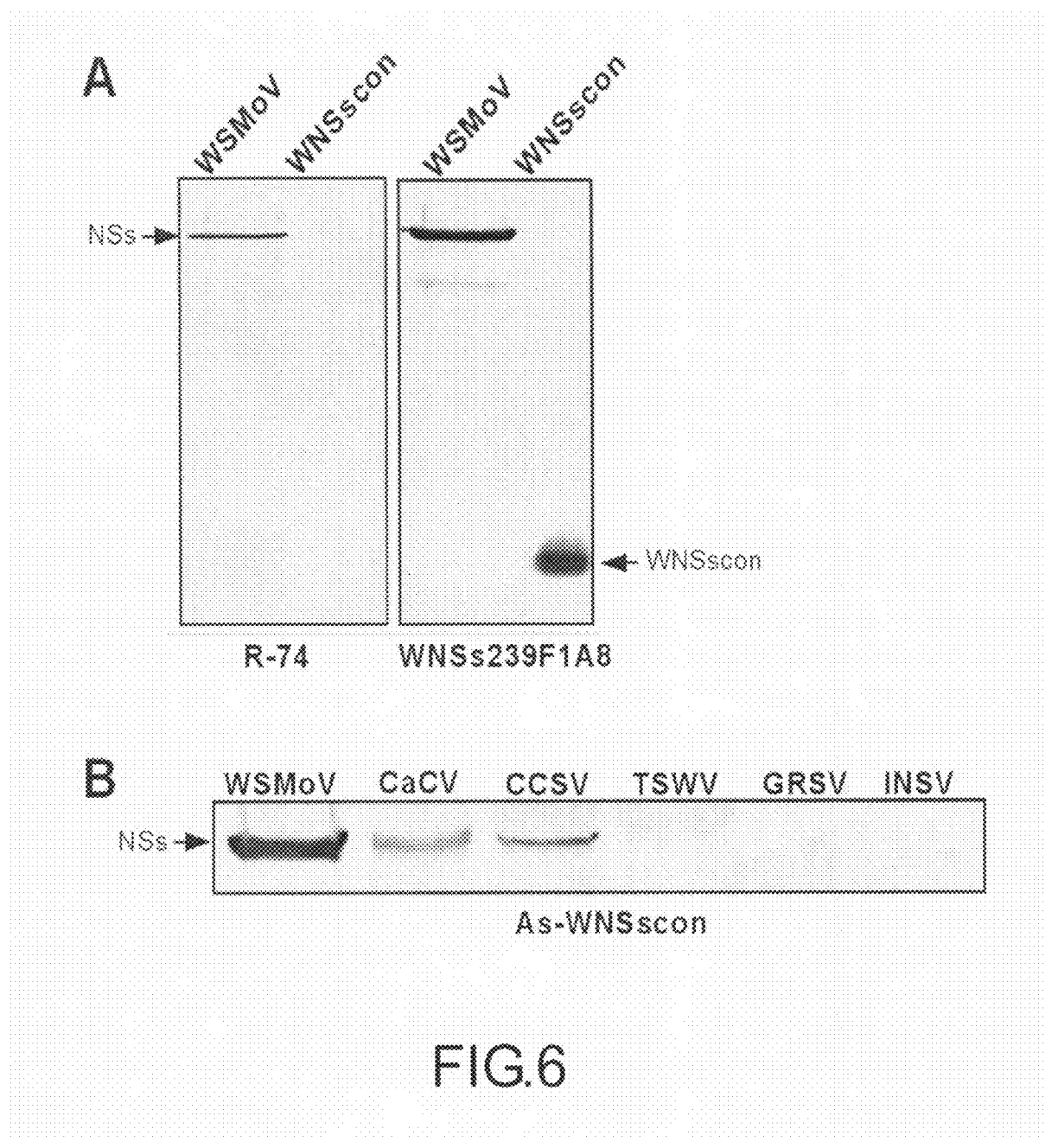

The rabbit antiserum against the synthetic peptide SEQ ID No.19 reacted positively with crude NSs antigens of WSMoV, CaCV and CCSV, but not with those of TSWV, GRSV, INSV and PCFV (FIG. 6B). Our results indicate that tospoviral NSs proteins of WSMoV serogroup share a conserved sequence at the N-terminal region, and that the antiserum raised from the consensus aa 98 to 120 synthetic peptide of NSs proteins recognized all tested members of the WSMoV serogroup.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A hybridoma cell line deposited under CCTCC accession number 200718.

2. A monoclonal antibody produced by the hybridoma cell line of claim 1, said monoclonal antibody binds to peptide SEQ ID No. 19.

3. A kit for detection of *tospovirus* species in the genus *Tospovirus* comprises a secondary antibody, washing solution, chromogenic substrate, and the monoclonal antibody of claim 2.

4. The kit of claim 3, wherein said secondary antibody is an enzyme conjugated anti-mouse IgG.

* * * * *

SEQUENCE LISTING

<160> NUMBER OF SEQ ID NOS: 19

<210> SEQ ID NO 1
<211> LENGTH: 37
<212> TYPE: DNA
<213> ORGANISM: Artificial
<220> FEATURE:
<223> OTHER INFORMATION: synthesized

<400> SEQUENCE: 1
gggtaccgca tgcatgtcta ctgcaaagaa tgctgct					37

<210> SEQ ID NO 2
<211> LENGTH: 34
<212> TYPE: DNA
<213> ORGANISM: Artificial
<220> FEATURE:
<223> OTHER INFORMATION: synthesized

<400> SEQUENCE: 2
ggcatgcttc tgcgagcatg aaatgaactt aatt					34

<210> SEQ ID NO 3
<211> LENGTH: 35
<212> TYPE: DNA
<213> ORGANISM: Artificial
<220> FEATURE:
<223> OTHER INFORMATION: synthesized

<400> SEQUENCE: 3
gggcatgcgg tgtgaagaac acaggctgca agttc					35

<210> SEQ ID NO 4
<211> LENGTH: 33
<212> TYPE: DNA
<213> ORGANISM: Artificial
<220> FEATURE:
<223> OTHER INFORMATION: synthesized

<400> SEQUENCE: 4
gggcatgcaa cacaggctgc aagttcacaa tgc					33

<210> SEQ ID NO 5
<211> LENGTH: 33
<212> TYPE: DNA
<213> ORGANISM: Artificial
<220> FEATURE:
<223> OTHER INFORMATION: synthesized

<400> SEQUENCE: 5
gggcatgcac aggctgcaag ttcacaatgc aca      33

<210> SEQ ID NO 6
<211> LENGTH: 35
<212> TYPE: DNA
<213> ORGANISM: Artificial
<220> FEATURE:
<223> OTHER INFORMATION: synthesized

<400> SEQUENCE: 6
gggcatgctg caagttcaca atgcacaatc aaatc      35

<210> SEQ ID NO 7
<211> LENGTH: 33
<212> TYPE: DNA
<213> ORGANISM: Artificial
<220> FEATURE:
<223> OTHER INFORMATION: synthesized

<400> SEQUENCE: 7
gggcatgctt cacaatgcac aatcaaatct tta      33

<210> SEQ ID NO 8
<211> LENGTH: 33
<212> TYPE: DNA
<213> ORGANISM: Artificial
<220> FEATURE:
<223> OTHER INFORMATION: synthesized

<400> SEQUENCE: 8
gggcatgcac aatgcacaat caaatcttta atc      33

<210> SEQ ID NO 9
<211> LENGTH: 35
<212> TYPE: DNA
<213> ORGANISM: Artificial
<220> FEATURE:
<223> OTHER INFORMATION: synthesized

<400> SEQUENCE: 9
gggcatgcaa tcaaatcttt aatccaaatt ccaat      35

<210> SEQ ID NO 10
<211> LENGTH: 37
<212> TYPE: DNA
<213> ORGANISM: Artificial
<220> FEATURE:
<223> OTHER INFORMATION: synthesized

<400> SEQUENCE: 10
gggtaccgca tgcatgacgc ccggaacaat ttcagaa      37

<210> SEQ ID NO 11
<211> LENGTH: 37
<212> TYPE: DNA
<213> ORGANISM: Artificial
<220> FEATURE:
<223> OTHER INFORMATION: synthesized

```
<400> SEQUENCE: 11
gggtaccgca tgcgaagggg ctttcgcaag gactttc                              37

<210> SEQ ID NO 12
<211> LENGTH: 33
<212> TYPE: DNA
<213> ORGANISM: Artificial
<220> FEATURE:
<223> OTHER INFORMATION: synthesized

<400> SEQUENCE: 12
ggcctaggat gacgcccgga acaatttcag aag                                  33

<210> SEQ ID NO 13
<211> LENGTH: 31
<212> TYPE: DNA
<213> ORGANISM: Artificial
<220> FEATURE:
<223> OTHER INFORMATION: synthesized

<400> SEQUENCE: 13
gcctagggaa ggggctttcg caaggacttt c                                    31

<210> SEQ ID NO 14
<211> LENGTH: 31
<212> TYPE: DNA
<213> ORGANISM: Artificial
<220> FEATURE:
<223> OTHER INFORMATION: synthesized

<400> SEQUENCE: 14
gggtaccgca ctcatccaaa caccatcccg a                                    31

<210> SEQ ID NO 15
<211> LENGTH: 31
<212> TYPE: DNA
<213> ORGANISM: Artificial
<220> FEATURE:
<223> OTHER INFORMATION: synthesized

<400> SEQUENCE: 15
gggtaccctc attactgttg tcagcaacag t                                    31

<210> SEQ ID NO 16
<211> LENGTH: 31
<212> TYPE: DNA
<213> ORGANISM: Artificial
<220> FEATURE:
<223> OTHER INFORMATION: synthesized

<400> SEQUENCE: 16
gggtaccttc tgctttcaca acaaagtgct g                                    31

<210> SEQ ID NO 17
<211> LENGTH: 35
<212> TYPE: DNA
<213> ORGANISM: Artificial
<220> FEATURE:
<223> OTHER INFORMATION: synthesized

<400> SEQUENCE: 17
ggcctaggtg ttatgtctag tccaaatttt tcaaa                                35

<210> SEQ ID NO 18
<211> LENGTH: 31
```

```
-continued

<212> TYPE: DNA
<213> ORGANISM: Artificial
<220> FEATURE:
<223> OTHER INFORMATION: synthesized

<400> SEQUENCE: 18
gcctagggca ctcatccaaa caccatcccg a                                31

<210> SEQ ID NO 19
<211> LENGTH: 16
<212> TYPE: PRT
<213> ORGANISM: Artificial
<220> FEATURE:
<223> OTHER INFORMATION: synthesized

<400> SEQUENCE: 19

Val Arg Lys Pro Gly Val Lys Asn Thr Gly Cys Lys Phe Thr Met His
1               5                   10                  15
```